United States Patent [19]

Fleischner

[11] Patent Number: 4,818,520

[45] Date of Patent: Apr. 4, 1989

[54] KERATIN HYDROLYSATE FORMULATIONS AND METHODS OF PREPARATION THEREOF

[75] Inventor: Albert M. Fleischner, Westwood, N.J.

[73] Assignee: Edmund M. Jaskiewicz, Washington, D.C.

[21] Appl. No.: 918,885

[22] Filed: Oct. 15, 1986

[51] Int. Cl.$^4$ .................. A61K 7/48; A61K 7/075; A61K 37/12; A61K 37/18

[52] U.S. Cl. .................................... 424/61; 424/63; 424/70; 424/73; 514/21; 514/846; 514/847; 530/357; 252/DIG. 13

[58] Field of Search ............... 424/61, 63, 65, 70, 424/73; 252/DIG. 13, 21; 514/844, 846, 847; 530/357, 353

[56] References Cited

U.S. PATENT DOCUMENTS

| | | | |
|---|---|---|---|
| 2,993,794 | 7/1961 | Moshy | 530/357 |
| 3,033,755 | 5/1962 | Jacobi | 514/21 X |
| 3,483,008 | 12/1969 | Herr | 424/65 X |
| 3,483,289 | 12/1969 | Michaelson et al. | 424/61 |
| 3,787,337 | 1/1974 | Goodwin | 530/357 X |
| 4,423,032 | 12/1983 | Abe et al. | 424/70 |
| 4,436,722 | 3/1984 | Matsunaga et al. | 424/70 |
| 4,495,173 | 1/1985 | Matsunaga et al. | 424/70 |
| 4,591,497 | 5/1986 | Naito et al. | 424/43 |

FOREIGN PATENT DOCUMENTS 1111934  5/1968  United Kingdom ............... 424/61

*Primary Examiner*—George F. Lesmes
*Assistant Examiner*—Susan S. Rucker
*Attorney, Agent, or Firm*—Edmund M. Jaskiewicz

[57] ABSTRACT

Keratin protein hydrolysate products, which are prepared from keratin-containing animal parts, such as fowl feathers and the like, the product being useful as an anti-skin blemisher, moisturizer, skin mask, shampoo enhancer, shaving lotion and nail hardener and conditioner, and method of preparation of the products.

6 Claims, No Drawings

KERATIN HYDROLYSATE FORMULATIONS AND METHODS OF PREPARATION THEREOF

FIELD OF THE INVENTION

This invention relates to keratin hydrolysate complexes with naturally occurring amino acids cystine-cysteine; the keratin derived modified protein being referred to hereinafter throughout the specification as KDMP. The hydrolysate keratin product is prepared by alkaline hydrolysis of a fibrous keratin which contains a family of structurally related water soluble peptides.

BACKGROUND AND SUMMARY OF THE INVENTION

It is an object of the present invention to provide a process and product whereby animal parts containing keratin, such as chicken, poultry, or other avian feathers, nails, beaks, and cattle or other animal horns, hooves and hair, are converted into KDMP complexes useful for topical application to human skin and nails to condition the same as hereinafter described.

Water soluble peptides present in fibrous keratin, on the average, contain fewer than ten amino acids, and under the conditions of the hydrolysis a number of the component amino acids are subject to chemical modification other than cleavage of peptide bonds. Amino acid analysis reveals an abundance of acidic and neutral amino acids as well as the presence of cystine and its oxidation products, most important of which is cysteine. An amber colored pigment exhibiting both cationic and hydrophobic properties is associated with the protein component.

Of the peptides obtained in the initial hydrolysate, in accordance with this invention, approximately 20% exhibit adsorption during a chromatography hydrophobic chromatographic support. During subsequent formulation steps an increasing number of the more polar peptides is lost, such that approximately 90% of the peptides present in the final formulation exhibit hydrophobic properties. Summarily, the protein component is composed of a family of structurally related low molecular weight peptides exhibiting both anionic and hydrophobic properties and containing the amino acid cystine.

The presence of naturally occurring cystine-cysteine has been found to be of particular importance in order to provide a product which is free from unpleasant odors. Where cysteine-cystine itself (unnatural) is added, it has been observed that there is a strong tendency for auto-oxidation and decomposition to occur and which produces a product having an unpleasant odor. Whereas, naturally derived or occurring cystine-cysteine obtained from KDMP, and produced as hereinafter described, is stable. The particular characteristic is explained by its reactivity, particularly its redox behavior (cysteine-cystine) which is of fundamental importance in cellular processes. The cystine in KDMP interacts with the abundant disulphide bridges present in keratin, found in the skin, hair and nails, thus markedly influencing the suppleness and elasticity of the skin treated. Apart from the direct improvement in the mechanical properties of the skin, the cystine also exhibits a stimulating effect on the metabolism of the epidermis.

It is known with respect to protein components of hair follicles, for example, that they are hydrophobic in nature and contain numerous sulfhydryl amino acid residues. Further, under the neutral or alkaline conditions, in accordance with this invention, cysteine reduction is accelerated in the presence of sulfhydryl containing compounds. Moreover, since the protein component of the present formulation, which contains a natural quantity of cystine, it serves as a thiol reducing reagent, thus increasing the cystine content of the hair. The peptides are absorbed by the hair, and it has been found that their affinity for a hydrophobic surface is favorably affected. These two independent phenomena acting in concert result in the formulation of a proteinaceous film which increases surface solubility, and protects the impact of environmental factors on the hair. The enhanced highlights observed with light reflecting hair colors also is attributed to the presence of a proteinaceous film which is a desirable attribute.

In addition, it has been observed that when utilizing the products of this invention, and wherein skin and nails are treated during the process with hot air flow drying, it results in the acceleration of cystine oxidation. Inasmuch as cystine associated with the protein component is absorbed by the hair, the oxidation results in the formation of cysteine molecular bridges between the hair follicle and proteinaceous film; thus stabilizing the film and producing a relatively hard and tough resistant surface on the skin or nail being treated.

DESCRIPTION OF THE PREFERRED EMBODIMENTS

The present invention is particularly illustrated by the following examples. In these examples, the keratin protein material is in the form of powder or meal commonly referred to as feathermeal. It should be understood, however, that even though the animal parts are generally cleansed to some extent prior to partial hydrolysis, it is possible and in fact quite often probable that associated non-keratin bearing parts are not removed from the keratin bearing parts. Thus, such material as blood, chicken feet, chicken heads and visera, as well as cattle legs and skin may be mixed with the desirable keratin bearing animal parts.

EXAMPLE 1

KDMP Product

A round-bottomed flask containing 166 ml. of water is heated to near reflux. To the hot water, 20 grams of strontium hydroxide is added. When the strontium hydroxide is completely dissolved, 20 grams of dry weight feathermeal is added. Where the feathermeal comprises excess fat, the feathermeal is initially washed with acetone or the like fat-solvent material. The mixture is then refluxed for approximately twenty hours at 100 degrees C. under one atmosphere of pressure. Thereafter, the solution is cooled and filtered to recover the hydrolysate, which is then reduced to a pH of 3.0 with a 15% solution of sufuric acid. The precipitate which forms during neutralization is removed by vacuum filtration. The tea-colored solution at pH 3.0, and constituting the KDMP complex, is then heated to near boiling and evaporated to ½ its original volume. The resultant concentrated viscous liquid is brought to pH 7.0 with 1N. sodium hydroxide solution. This neutralized viscous liquid proteinaceous extract is stored for about seven days at room temperature (22-25 degrees C.). At the end of the storage time, the extract is heated and all precipitate material re-dissolved. The final KDMP product is a clear viscous liquid which was found to inhibit microbial growth after incubation at room temperature (approx. 25 degrees C.) for 72 hours. The KDMP bactericidal product is useful as a skin mask, anti-blemish skin conditioner, moisturizer, and skin deodorant.

EXAMPLE 2

Concentrated KDMP Product

A one-liter round-bottom was filled with 249 ml. of water (deionized water was used) and the water was heated to approximately 80 degrees C. To the hot water 30 g. of strontium hydrate were added. Next, the dry weight equivalent of 30 g. of feathermeal as described in Example 1, were added. (On an average summer day in a temperate climate, feathermeal might contain 10–15% moisture. Accordingly, additional feathermeal was added to compensate for the moisture content.) The mixture was then refluxed for eight hours at sea level pressure (1 atmosphere).

The solution was allowed to cool in the flask (pH at 11–12.5). A 50% solution of sulfuric acid was added to reduce the in-flask pH to 8.5 to 9.0 (approximately 2 ml. of 50% $H_2SO_4$.) The solution was filtered (filter cake discarded) and stored at room temperature for 48 hours.

The filtrate was brought to pH 6.8–7.0 with additional 50% sulfuric acid (approximately 2–3 ml.). The pH 6.8–7.0 filtrate was filtered after sitting at room temperature for two hours with a final KDMP filtrate of pH 7.0.

The final KDMP filtrate at pH 7.0 was evaporated by heating and stirring to one-half of its original volume. A portion of the concentrated KDMP (100 ml.) was mixed with 150 ml. of pure methanol (>95%). The resultant white milky mixture was allowed to stand at room temperature for 24 hours. After 24 hours the mixture had separated into a straw colored upper phase and white lower phase. The upper phase was decanted and the white lower phase retained as the finished product which is useful as a shampoo enhancer, shaving lotion and nail hardener and conditioner.

EXAMPLE 3

KDMP Detergent Type Shampoo

A detergent mixture comprising (by volume) 5% coconut diethanolamide and 95% modified alkylolamide is diluted with deionized water by adding 5 volumes of water to each volume of the detergent mixture. The diluted detergent is then allowed to stand for approximately 18 hours or until all air bubbles are removed. Thereafter, to the diluted detergent mixture is added 1 part of concentrated KDMP, as described in Example 2. To this detergent-KDMP mixture is admixed 2 parts water to provide a product having one volume of diluted detergent one volume of KDMP, and which mixture, when stored for 16–18 hours separates into two phases. The resultant precipitate phase is removed by filtration to recover a heavy viscous bottom phase solution.

To produce the shampoo product, three different preservatives may be used such as Methyl paraben (methyl-p-hydroxybenzoate) at a concentration of 0.2 percent of the total volume of shampoo being produced. Methyl paraben is dissolved in the detergents. Propyl paraben (propyl-p-hydroxybenzoate) at a concentration of 0.12 percent of the total volume of shampoo being produced. Propyl paraben is dissolved in the water used for formulation. Mercaptoethanol (ME) at a concentration of 0.1 percent of the total volume of shampoo being produced. ME is added to the formulation as the final ingredient.

In the production of a shampoo wherein methyl paraben preservative is added to the above-described bottom phase solution, the mixture consists of four parts (by volume) of the bottom phase solution and one part of concentrated KDMP. To the resultant mixture two parts of water is introduced to produce the final shampoo product. Where other preservatives are utilized, for example, mercaptoethanol, it is added as a final step and uniformly mixed into the mixture to provide the shampoo product. Where it is deemed unnecessary, or not desired, no preservative need be introduced in formulating the shampoo.

The detergent shampoo product, with or without a preservative, may be utilized as a shampoo enhancer, for example, admixed with other shampoo products, or as a lotion, such as a shaving cream or skin conditioner or as refresher, or as a nail hardener and toughening of film nail conditioner. When the keratin protein cystine-cysteine enriched shampoo is used as an enhancer, e.g., in conjunction with another shampoo, it has been found to improve the body and luster of hair, improve the clarity and reflectivity of the hair's natural highlights, reduce split ends, and observable hair loss on the brush. This use of applicant's new preparation, i.e. as an enhancer, means that the preparation is added to or used in conjunction with a shampoo to improve or enhance the final shampoo product.

Its high substantivity results in additional retardation of water loss from the hair strands reducing brittleness and breakage. It fills in irregularities in the hair strands, providing fuller, stronger and more uniform strands of hair.

It also has excellent cleansing characteristics, helping the shampoo itself to leave the hair with a longer lasting, "squeaky clean" shampooing effect, with no shampoo build-up.

EXAMPLE 4

Alkaline Hydrolysate Preparation

A roundbottom flask with 996 ml. of water is heated. To the hot water, 120 grams of strontium hydrate (hydroxide) is added. Next, 120 grams of dry weight feathermeal is added. The mixture is then refluxed for eight hours at 100 degrees C. at a pressure of 1 atmosphere.

The cooled solution (pH 11–12.5) is then brought to pH 8.8 to 9.0 with a 15 percent solution of sulfuric acid, and filtered. The resultant alkaline hydrolysate solution at pH 8.8–9.0 can be stored at room temperature and is stable for a period of at least five months.

EXAMPLE 5

Preparation of Concentrated KDMP (clear solution)

The alkaline hydrolysate of Example 4 is reduced to pH3.0 with the addition of a 15 percent solution of sulfuric acid. The resultant precipitate is removed by vacuum filtration, and the acidified hydrolysate (KDMP) is stored in a covered container for a minimum of two days and up to five days. After the storage period the KDMP is again filtered. The filtrate KDMP at pH 3.0 is heated to boiling and evaporated to one-half of its original volume. The resultant liquid is brought to pH 7.0 with 1 N.-NaOH. This neutralized solution is again reduced to pH 3.0 with the addition of 15 percent sulfuric acid. The resultant heavy viscous fraction is removed by filtration and the clear solution is recovered and returned to a pH 7.0 with 1 N. NaOH. The final product at pH 7.0 is concentrated KDMP as a clear solution.

EXAMPLE 6

KDMP and Detergent Partition Formulation

A mixture of 5 percent coconut diethanolamide and 95 percent modified alkylolamide is prepared. The detergent mixture is diluted with dionized water by adding 5 volumes of water to each volume of mix detergent. This diluted detergent mixture is allowed to stand for approximately 18 hours or until all bubbles are removed. The diluted detergents are next mixed with concentrated KDMP (of Example 2), the KDMP mixture consisting of one part by volume of diluted detergent to one volume of KDMP. The two phases separate within 6–18 hours and a bottom layer (50–60% volume) is recovered, the top layer being discarded.

To the bottom layer, a number of preservatives are added as follows:

Methyl paraben (methyl-p-hydroxybenzoate) is added at a concentration of 0.25 percent of the total volume of the formulation being produced. Methyl paraben is dissolved in the detergents.

Propyl paraben (propyl-p-hydroxybenzoate) is added at a concentration of 0.10 percent of the total volume of the formulation being produced. Propyl paraben is dissolved in the water used for formulation.

Germal 115 (Imidazolidinyl Urea) 0.07 grams per ounce is added at a concentration of 0.25%.

In this formulation, a mixture of preservatives is utilized and which comprise modified alkylolamide, triethanolzmine salt of normal dodecylbenzene sulfonic acid and coconut diethanolamide in a ratio of 8.5:3:0.5 and wherein 0.5 represents 50 ml., 3 represents 300 ml., and 8.5 equals 850 ml. for a total volume of 1200 ml. Methyl paraben is dissolved in this detergent mixture. To this detergent mixture 4 parts (400 ml.) of the bottom phase and 1 part (100 ml.) from above are combined. To this mixture 2 parts (200 ml.) of water are added. Where parabens are being used as preservatives, propyl paraben and Germal 115 are dissolved in the water prior to its addition to the formulation. The resultant product is the final formulation with the preservatives.

The detergent KDMP product is particularly useful as a hair and nail conditioner such as that described in Example 3. Further, inasmuch as keratins have a close structural relationship to human hair, skin and nails, and the natural cystine contained in KDMP, the products of this invention are especially useful for conditioning hair, skin and nails. With respect to nails, for example, the inventive product conditions and helps to prevent the nail from drying out and becoming brittle. Current data indicates that the spaces occurring from normal wear and tear on the surface of the nail are filled in by the product's strong proteinaceous film which also enables the product to adhere strongly to the nail surface. Splitting and peeling of the nail layers is reduced while hardness (thickness) is enhanced, brittleness is reduced, and moisture is retained, making the nail more supple.

The product of the invention does not require or contain coloring agents or formaldehyde, such as are commonly found in related products.

EXAMPLE 7

Non-concentrated KDMP

For use in the preparation of various KDMP products, in accordance with this invention, the alkaline hydrolysate solution, as described in Example 4, is brought to a pH of 3.0 by the addition of a 15% solution of sulfuric acid and the resultant precipitate formed removed by vacuum filtration. The acidified hydrolysate solution is thereafter stored in a closed container for approximately five days. Afer the storage period the hydrolysate solution is again filtered to recover a filtrate constituting the non-concentrated KDMP product, and which is preferably utilized in the preparation of the KDMP product within 18 to 24 hours.

Whereas the keratin modified protein products of the invention are adapted for use on natural nails as a hardener and conditioner, it may also be applied, likewise, over lacquer nail polishes where the nail surface is free to receive the same as a tough flexible film coating.

While this invention has been described in detail with particular reference to preferred embodiments thereof, it will be understood that variations and modifications can be effected within the spirit and scope of the invention as described hereinbefore and as defined in the appended claims.

What is claimed is:

1. The method of preparing a neutralized viscous liquid proteinaceous extract which is useful as a skin conditioner, shampoo and the like, comprising the steps of heating an aqueous mixture of avian feathermeal and alkaline material; refluxing said mixture for several hours at 100 degrees C. under one atmosphere of pressure; thereafter cooling the refluxed solution and filtering said solution to recover a proteinaceous extract; adding sufficient sulfuric acid to extract to reduce the pH to 3.0; removing the precipitate formed during acidification of the extract by vacuum filtration; then heating and evaporating approximately one half by volume of the resultant concentrated viscous filtrate; adding sufficient alkali hydroxide to said viscous filtrate to neutralize the same to a pH of 7.0; and finally storing said proteinaceous extract at room temperature, and thereafter re-heating the said extract to re-dissolve precipitate material to produce a clear viscous liquid lotion.

2. The method of claim 21 wherein the alkaline reflux solution comprises strontium hydroxide.

3. The method of claim 21 wherein the alkaline reflux extract material comprises a fibrous keratin which contains water soluble peptides.

4. The method of claim 21 wherein the viscous liquid is admixed with detergents and methyl parabin.

5. The method of claim 21 wherein the viscous liquid comprises a mixture of detergents and preservatives.

6. The method of claim 21 wherein the proteinaceous extract material comprises a naturally occurring cystine-cysteine.

* * * * *